United States Patent [19]

Fialla

[11] Patent Number: 5,110,994
[45] Date of Patent: May 5, 1992

[54] PROCESS FOR SYNTHESIZING 9,9-BIS-(HYDROXYPHENYL)FLUORENE

[75] Inventor: Peter Fialla, Maria Enzersdorf, Austria

[73] Assignee: ISONOVA Technische Innovationen Ges.m.b.H., Austria

[21] Appl. No.: 613,668

[22] PCT Filed: Apr. 17, 1990

[86] PCT No.: PCT/AT90/00031
§ 371 Date: Dec. 10, 1990
§ 102(e) Date: Dec. 10, 1990

[87] PCT Pub. No.: WO90/12776
PCT Pub. Date: Nov. 1, 1990

[30] Foreign Application Priority Data

Apr. 17, 1989 [AT] Austria .................................. 901/89

[51] Int. Cl.$^5$ ...................... C07C 39/12; C07C 37/20
[52] U.S. Cl. ................................ 568/727; 568/719; 568/718; 568/722; 568/728
[58] Field of Search ............... 568/718, 719, 727, 728, 568/722

[56] References Cited

U.S. PATENT DOCUMENTS

| | | | |
|---|---|---|---|
| 2,775,620 | 12/1956 | Williamson | 568/727 |
| 4,024,194 | 5/1977 | Corn, Jr. | 568/719 |
| 4,048,200 | 9/1977 | Tresper et al. | |
| 4,049,721 | 9/1977 | Corn, Jr. et al. | 568/719 |
| 4,675,458 | 6/1987 | Riemann et al. | 568/727 |

FOREIGN PATENT DOCUMENTS 0065060 11/1982 European Pat. Off. .

Primary Examiner—Werren B. Lone
Attorney, Agent, or Firm—Bacon & Thomas

[57] ABSTRACT

The invention concerns a process for synthesizing 9,9-bis(hydroxyphenyl)fluorene by reacting fluorene with excess phenol using a liquid catalyst prepared by dissolving aluminum trichloride in an anhydrous organic solvent such as toluene evincing the property of an electron donor while hydrochloric-acid gas is being supplied. For the purpose of the synthesis, the fluorenone is dissolved for instance at 60° C. in the liquid phenol and then the liquid catalyst is dripped into the agitated reaction mixture at such a rate that the temperature of the reaction mixture is kept below 60° C. Following catalyst addition and subsequent after-reaction interval of several hours, the raw product is mixed with hot water and the excess phenol is removed by steam distillation. After signle-washing with water, the raw product is dissolved in hot acetone, allowed to crystallize, is filtered out and dried in vacuum. Lastly the raw product is recrystallized from 1,2-dichloroethane to form the pure product.

6 Claims, No Drawings

PROCESS FOR SYNTHESIZING 9,9-BIS-(HYDROXYPHENYL)FLUORENE

TECHNICAL FIELD

The invention concerns a process for making 9,9-vis(4-hydroxyphenyl)fluorene by reacting fluorenone with excess phenol in a condensation reaction while using hydrochloric-acid gas as the condensing agent and aluminum trichloride as the catalyst.

STATE OF THE ART

A method of this sort is known from the European patent document A 00 65 060 wherein the solid catalyst, for instance $AlCl_3$, is added to the reaction mixture and the hydrochloric-acid gas is introduced into the reaction mixture during the reaction. It is important in this respect that the temperature in the reaction vessel shall not exceed 60°–80° C. This method makes it possible to substantially impede formation of isomers of 9,9-bis(4-hydrophenyl)fluorene and of byproducts of higher condensation. However where synthesis batches in large vessels are concerned, this method incurs several process-technological drawbacks. One of these is that the solid, pulverulent catalyst ($AlCl_3$) cannot be kept in suspension in the reaction mixture but instead soon settles at the bottom of this vessel and there is then danger of clogging the bottom discharge valves. Moreover it is no simple matter to introduce the hydrochloric-acid gas over the time of reaction, which is several hours. Lastly the heat release in this known method—especially where large batches and increasing viscosities are concerned—can be controlled only poorly by means of wall cooling.

DESCRIPTION OF THE INVENTION

The object of the invention is to create a process of the initially cited kind that shall be free of the above drawbacks.

The basic problem of the invention is solved by the innovative process in that aluminum chloride is dissolved in an anhydrous organic solvent of mixture of solvents at least nearly inert relative to the condensation reaction, where this solvent or at least one component of the mixture of solvents evinces the property of electron donor, with simultaneous introduction of hydrochloric-acid gas, in order to prepare a liquid catalyst, and in that this liquid catalyst is dripped into the reaction mixture subjected to agitation, the temperature of the reaction mixture being kept below 60° C. during this dripping procedure by controlling the catalyst addition rate.

In an advantageous implementation of the process of the invention, the solvent or the component of the mixture of solvents is benzene or a substituted benzene, preferably toluene.

In another advantageous implementation of the invention, the solvent or the component of the mixture of solvents is an ether. This ether advantageously may be methyl-tert.-butylether.

ILLUSTRATIVE IMPLEMENTATION OF THE INVENTION

A) Substances Used 9,010 g (50 moles) of fluorenone of 99.0% purity with a melting point of 80°–82° C. and a density of 1.13 g/cm$^3$, 18,820 g (200 moles) of phenol (water content: 0.2%),
1,300 g (9.75 moles) of sublimated aluminum trichloride, hydrochloric-acid gas, anhydrous toluene.

B) Preparing the Liquid Catalyst

Three liters of anhydrous toluene and the stated amount of aluminum chloride are placed in a flask equipped with agitator. Next and at room temperature, hydrochloric-acid gas is introduced, in the presence of constant agitation, into the flask until the entire aluminum trichloride has dissolved and a two-phase, liquid system has been created. The supernatant phase consists mainly of toluene and the hydrochloric-acid gas dissolved therein.

C) Carrying Out the Synthesis

The solid fluorenone is placed in a 100-liter reaction vessel and is mixed with phenol heated to 60° C., that is in the liquid state, with agitation. The reaction mixture is heated to 40° to 50° C. Then, with further agitation, the liquid catalyst is slowly dripped in and thereby the temperature is kept at about 50° C. Dripping the catalyst requires about 1½ h.

After termination of catalyst addition, increase of the viscosity of the reaction mixture—from which the raw product already accumulates in part—is noted. After 4 to 5 h from the beginning of the reaction, 20 liters of hot water are added and thereupon the excess phenol is removed by steam distillation.

Following phase separation, the supernatant water is decanted and the raw product is washed with about 30 liters hot water, then is allowed to settle again and decanting proceeds again. The raw product so treated is dissolved with 30 liters acetone with reflux boiling. The acetone solution is cooled and an acetone adduct of 9,9-bis-(4-hydroxyphenyl)fluorene crystallizes. This crystalline acetone adduct is dried in a vacuum oven at 100° C. and at a pressure of 0.1 bars. The raw-product yield is 85–90% of theoretical for the described process.

This raw product is recrystallized from 1,2-dichloroethane. Then it is dissolved in dichloroethane with reflux and next is filtered by means of activated carbon. The pure product crystallized by cooling evinces a purity in excess of 99.8% and its yield is about 80% of theoretical.

The melting point of the pure 9,9-bis(4-hydroxyphenyl)fluorene measured by means of DSC as the onset temperature is 225.5° C.

Commercial Applicability

The 9.9-bis(4-hydroxyphenyl)fluorene prepared by the process of the invention is advantageously used as a monomer for the production of high-temperature resistant aromatic polyesters, similarly to the procedure elucidated in the European patent document A 00 65 060.

I claim:

1. A process for preparing 9,9-bis(4-hydroxyphenyl)-fluorene by reacting fluorenone with excess phenol in a condensation reaction using hydrochloric acid gas as the condensing agent and aluminum trichloride as the catalyst, comprising preparing a liquid catalyst by dissolving aluminum trichloride in an anhydrous organic solvent or mixture of solvents which are substantially inert relative to the condensation reaction, the solvent or at least one component of the mixture of solvents being an electron donor, while simultaneously introducing hydrochloric acid gas and introducing this liquid catalyst by dripping into the reaction mixture under agitation.

2. The process defined by claim 1, wherein the solvent or a component of the mixture of solvents is benzene or a substituted benzene.

3. The process as defined in claim 2, wherein said substituted benzene is toluene.

4. The process as defined in claim 1, wherein the solvent or a component of the mixture of solvents is an ether.

5. The process as defined in claim 4, wherein said ether is methyl-tert-butylether.

6. The process as defined in claim 1, further comprising maintaining the temperature of the reaction mixture during the introduction of the liquid catalyst below 60° C. by controlling the rate of introduction of the catalyst.

* * * * *